US006241756B1

United States Patent
Kappel

(10) Patent No.: US 6,241,756 B1
(45) Date of Patent: Jun. 5, 2001

(54) UPPER BODY WARMING BLANKET

(75) Inventor: Thomas F. Kappel, St. Louis, MO (US)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 08/263,853

(22) Filed: Jun. 21, 1994

(51) Int. Cl.$^7$ ....................................................... A61F 7/00
(52) U.S. Cl. .............................. 607/107; 607/104; 5/423; 62/259.003
(58) Field of Search ................................... 607/104, 107, 607/114; 62/259.003; 5/423

(56) References Cited

U.S. PATENT DOCUMENTS 5,300,102 * 4/1994 Augustine et al. .................. 607/107
5,304,213 * 4/1994 Becke et al. ........................ 607/114
5,324,320 * 6/1994 Augustine et al. .................. 607/167
5,350,417 * 9/1994 Augustine ............................ 607/104

\* cited by examiner

Primary Examiner—Robert L. Nasser
(74) Attorney, Agent, or Firm—Rothwell, Figg, Ernst & Manbeck

(57) ABSTRACT

The present invention relates to an upper body blanket for use with forced air convection systems, wherein the blanket includes an integrally formed head cover and integrally formed tie straps. By providing a blanket with a head cover, heat loss from the head area of the patient can be significantly reduced.

13 Claims, 2 Drawing Sheets

UPPER BODY WARMING BLANKET

BACKGROUND

Hypothermia is a condition of subnormal body temperature which presents serious consequences to the patient suffering therefrom. It has been shown that nearly seventy five percent of all patients who undergo surgical procedures develop hypothermia. This equates to approximately fourteen million patients a year in the United States alone. The hypothermic condition is brought on by many factors including anesthesia, the air conditioning of the operating room, and the infusion of cold blood, I–V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling air flow from an inlet port. Non-inflatable portions were provided around the periphery of the blanket to secure the blanket around the body.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto.

In U.S. Pat. No. 4,572,188 to Augustine et al, a forced air convection system which can supply either cool or warm air to a blanket is described. The blanket in Augustine et al comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. No. 4,660,388 to Greene, Jr.; U.S. Pat. No. 4,777,802 to Feher; and U.S. Pat. No. 4,867,230 to Voss. Each of these patents describe blankets having various attributes and configurations to supply cool or warm air to the person.

While some of the above systems suggest use in the operating room, there are a number of disadvantages associated with such use. For example, it is often necessary to have access to a particular area of the body for surgery. A full body blanket can interfere with this access.

Therefore, there is a need in the art for improvements to blankets for forced warm air convection systems.

OBJECT OF THE INVENTION

It is one object of the present invention to provide a blanket for a forced warm air convection system which covers the upper body of the patient.

It is another object of the present invention to provide a blanket for a forced warm air convection system which includes an integral head cover.

SUMMARY OF THE INVENTION

The above objects and others are accomplished according to the present invention by providing a blanket for a warm air convection system having various optimal features as will be discussed in detail below.

DETAILED DESCRIPTION OF THE INVENTION

Figure 1:
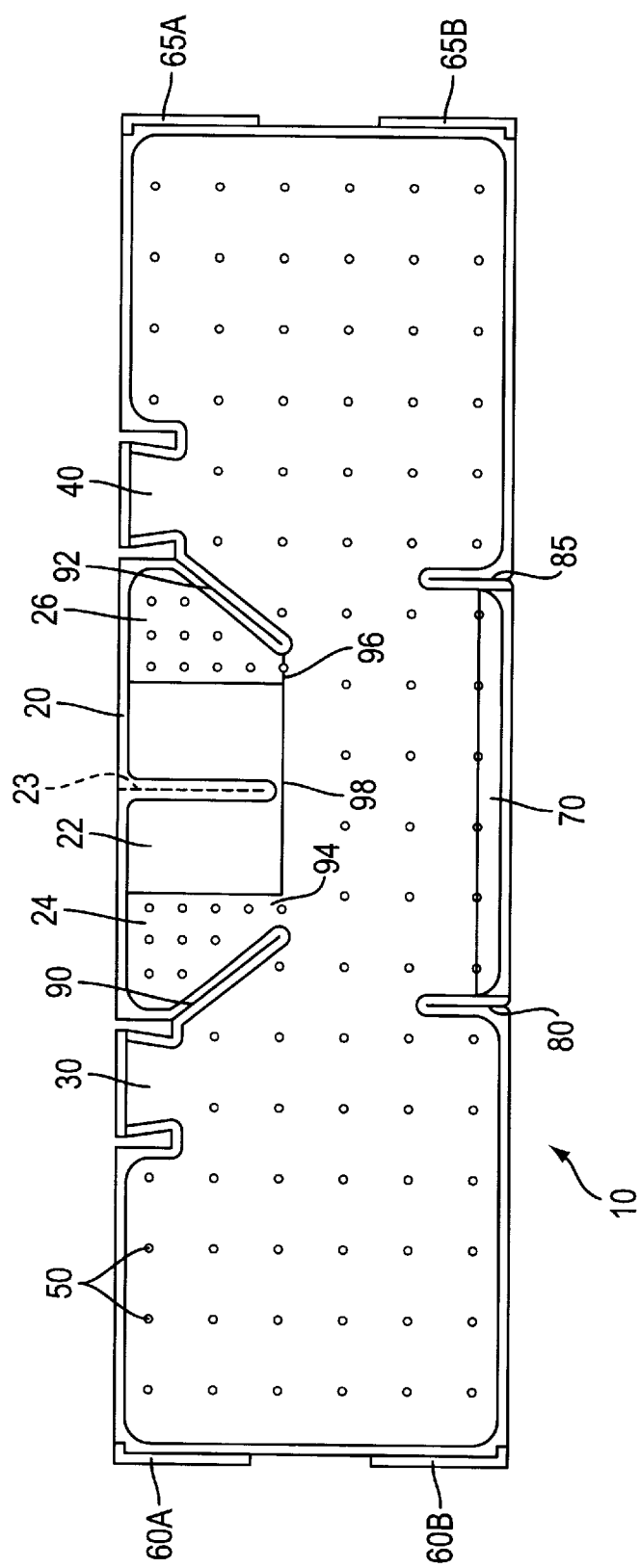
FIG. 1 is a plan view of a blanket for a forced warm air convection system according to one embodiment of the present invention, wherein a head cover is shown in an initial position.
Figure 2:
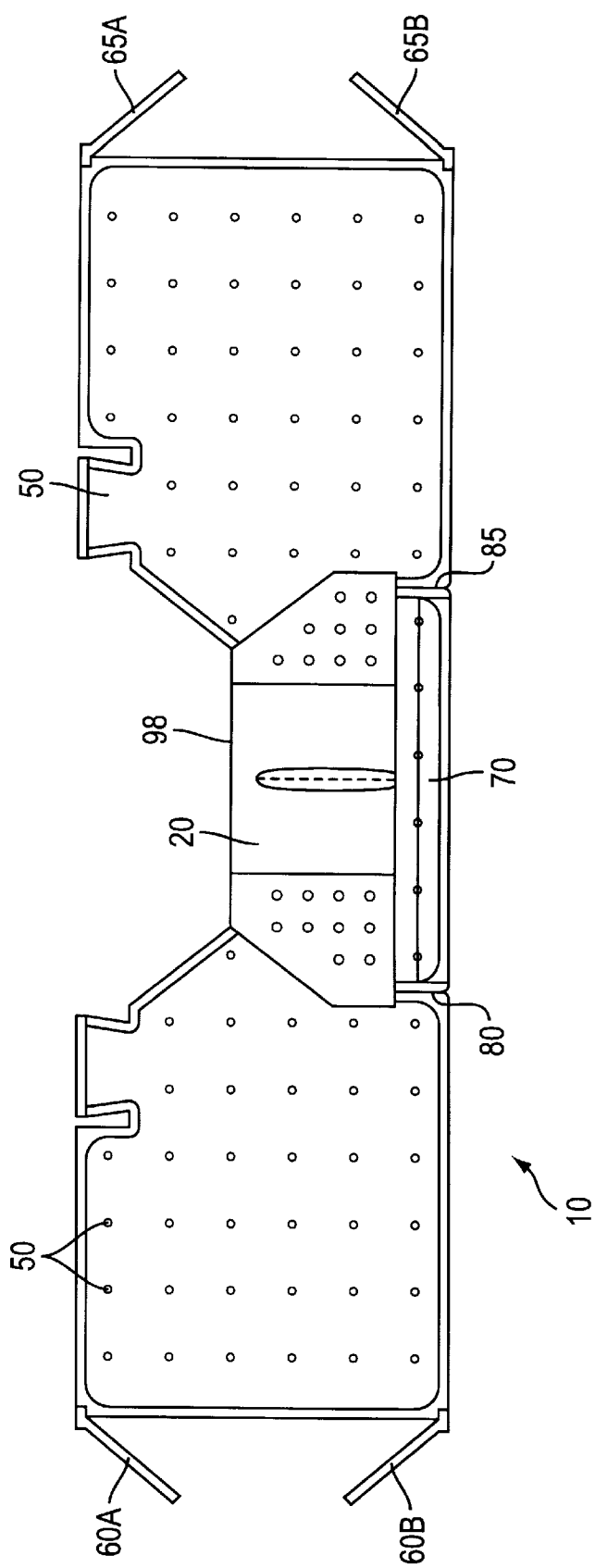
FIG. 2 is a plan view of the blanket shown in FIG. 1, wherein a head cover is shown in a second position, and tie straps are shown ready for use.

FIG. 1 and FIG. 2 are plan views of the blanket according to the present invention, showing the blanket in different states of readiness for use. Like reference numerals are used to identify like parts of the blanket in FIG. 1 and FIG. 2.

FIG. 1 is a plan view of a blanket, generally designated by reference numeral 10, for a forced warm air convection system, wherein the blanket 10, is appropriate for use in the operating room. The blanket 10, shown in FIG. 1 is an upper body blanket, designed to cover the upper body portions of a patient who is undergoing a surgical procedure to lower body portions. The blanket, 10, has a generally rectangular shape and comprises two sheets of material which are sealed together along their peripheral edges and are connected together at connection spot welds 50, discretely located on the interior surface portions of the sheets. By connecting the sheets of the blanket 10, in this manner, the blanket 10, may be inflated by supplying air to the interior area formed between the sheets of material.

The blanket 10, further includes a first inlet port 30, and a second inlet port 40. Inlet ports 30, 40 are in communication with the interior of the blanket 10, and may be used to supply air to the interior of the blanket 10, so as to inflate blanket 10. The lower surface (not shown) of the blanket 10, is provided with a plurality of small exit ports to allow warm air to escape from the blanket 10, toward a patient.

It has been recognized that the head is a major contributor to heat loss from the body. Therefore, the blanket 10, according to the present invention, includes a head cover 20, which can be used to directly or indirectly warm the head of the patient during surgery. The head cover 20, has a funnel or "U" shape and may be formed from the same multilayer quilted material as the rest of the blanket 10. Alternatively, the head cover 20, may be a single layer of material or may be a combination of multilayer and single layer construction. In FIG. 1, the head cover 20, is shown in an initial position as would be supplied. In a preferred embodiment as shown in FIG. 1, head cover 20, includes a center portion 22, of a single sheet separated by a perforated slit 23. Inflatable wing portions 24 and 26, lie to either side of center portion 22, and are separated from the main body of blanket 10, by slits 90 and 92. In the position shown in FIG. 1, the head cover 20, will extend over the head of a patient. The perforated slit 23, may be opened to allow for positioning of the head cover 20, around medical tubes, such as a tracheal tube exiting from the mouth or nose of a patient.

In FIG. 2, the head cover 20, is shown folded back along fold line 98, and overlying the main body of blanket 10.

The blanket 10, may further include a number of other useful features. In particular, integrally formed tie straps 60A, 60B, 65A, 65B, may be provided. Initially, the tie straps 60A, 60B, 65A, 65B, are an integral portion of the blanket 10, as shown in FIG. 1. The tie straps 60A, 60B, 65A, 65B, can be torn or cut apart from the blanket 10, as shown in FIG. 2 to be used to secure the blanket such as by tying the tie straps 60A, 60B, 65A, 65B, around another piece of equipment, e.g. a surgical arm board. Preferably, the tie straps 60A, 60B, 65A, 65B, are formed with perforations so as to allow for easy separation from the blanket 10.

In addition, blanket 10, includes an integrally formed piece of medical tape 70. This tape may be used to secure the blanket 10, to the patient and to isolate the turbulent air exiting the blanket 10, within the area covered by the blanket 10. This is advantageous in avoiding the chance of air escaping from the blanket 10, and blowing across the surgical site, which can be distracting to the surgeon and possibly cause contamination of the surgical site.

Moreover, blanket 10, includes two slits 80, 85, formed on the lower edge. These slits 80, 85, allow the blanket 10, to more easily conform to the patient's body when in use.

In use, the blanket 10, is placed over the upper body of a patient such that the inlet ports 30, 40, are oriented in a direction pointing toward the top of the head of the patient. In this position, one inlet port will be located on each side of the patient's head. The blanket 10, should be situated such that the bottom edge is roughly aligned with the patient's nipple line.

The inlet ports 30, 40, may initially be closed by any suitable means such as sealing, folding, taping, snapping, etc. In the case where the inlet has been permanently sealed, means such as a perforated tear strip may be provided to enable easy opening of the inlet port selected for use. However, such sealing of the inlet ports requires the user to select the inlet port to be used prior to operation of the blanket 10, and does not allow switching to the other inlet port during use. This is because once the permanent seal for such an inlet port has been broken or opened, it is not possible to re-close the inlet port.

Therefore, in a preferred embodiment, the inlet ports 30, 40 will be initially closed by means that allow re-closing. In particular, means such as an adhesive strip, double-sided tape, snaps, zippers, folding flaps, a ziplock type seal, velcro strips, etc. may be utilized.

As shown in FIG. 1, the head cover 20, will extend over the patient's head, and provide warming to the head area. Alternatively, as shown in FIG. 2, the head cover 20, may be folded back over the main body of blanket 10, if heating of the head area is not desired. The tie straps 60A, 60B, 65A, 65B, may be separated from the blanket 10, and tied to any suitable structure so as to secure the blanket 10, in place. The medical tape 70, is adhered to the patient to isolate the warming area below the blanket 10, and slits 80, 85, allow the blanket 10, to conform to the patient.

An inlet port is chosen for use and opened. A source of warm air is then connected to the selected inlet port and the blanket 10, is inflated. Warm air circulates within the confines of the blanket 10, and exits toward the patient through the perforations (not shown) through the lower layer of the blanket 10.

The head of the patient may be warmed in various ways depending on the configuration and construction of the head cover 20. In particular, if the head cover 20, is a single sheet, then air exiting from the inflated portion of blanket 10, will be trapped below the head cover 20, so as to provide indirect air warming to the head area. Alternatively, if the head cover 20, is a multisheet construction or a combination of single sheet and multisheet construction, then the head cover 20, may be inflated at the same time as the rest of blanket 10. In this case, the head cover 20, is preferably provided with exit perforations through its lower layer in order to provide direct convective air warming to the head area. If no perforations are provided, the inflated head cover 20, can still provide warming to the head area through heat conduction from the lower sheet thereof.

In the preferred embodiment shown in FIG. 1, the inflatable wing portions 24 and 25, are inflated at the same time as the main body of blanket 10, by warm air passing through inlet areas 94 and 96, to wing portions 24 and 25 respectively. Warming to the head area is then accomplished either by direct convective air warming through perforations (not shown) in the underside of wing portions 24 and 26, or by conduction from the underside of wing portions 24 and 26, if no perforations are provided. Center portion 22, also aids in the warming of the head area by trapping warm air exiting from other areas of blanket 10.

Alternatively as shown in FIG. 2, if no heating of the head area is desired, head cover 20, may be folded back along fold line 98. This fold will essentially close inlet areas 94 and 96, and wing portions 24 and 26 will not be inflated.

The blanket according to the present invention has several advantages. In particular, by providing a blanket with dual inlets, the user has the choice of positioning the air supply or blower unit and the supply hose on either side of the patient. In addition, by providing resealable inlet ports, the user may switch inlets during use. This is particularly advantageous in allowing the surgeon full access to the patient.

The provision of spot welds 50, to connect the separate sheets of the blanket 10, also is advantageous. In particular, the spot welds 50, allow the free flow of warm air in all directions and therefore allow for better heat distribution within the blanket. This can be critical in reducing the occurrence of hot or cold spots within the blanket during use.

The head cover helps in providing extra heat to the patient and in controlling the loss of heat from the head of the patient. As noted above, the surgical tape and tear strips secure the blanket and the slits provide for better conformance of the blanket to the patient.

The blanket may be formed of any suitable material capable of being sealed together at selected positions and having sufficient strength to allow inflation and adequate air distribution within the inflated portion. Such materials include plastics, non-woven wood pulp compositions, laminated plastic and wood pulp materials, and combinations thereof.

The dimensions of the blanket according to the present invention are as follows. The blanket length from side to side should be about 82 inches, while the length from top to bottom should be about 24 inches. The head cover should be about 18 inches wide and about 10 inches deep so as to fully cover the head area of a patient. The inlet ports may be provided almost anywhere along the blanket, but preferably are located along the upper edge of the blanket on either side of the head cover portion. The tie straps preferably extend along the ends of the blanket, and are about 8 inches in length when separated from the blanket. The medical tape should be provided along the middle portion of the bottom edge of the blanket and should extend for about 18 inches. The slits are preferable located along the bottom edge of the blanket on either side of the medical tape and are about 5 inches in length.

It should be noted that the present invention is primarily concerned with a blanket which can be used to supply warm air to a patient in the operating room during a surgical procedure, so as to help prevent the occurrence of hypothermia. However, it will be evident to one skilled in the art that the blankets according to the present invention could be used in areas other than the operating room, such as in the recovery room, or in the patient's regular hospital room. Further, it will be evident to one skilled in the art that a source of pressurized cooled air could be provided to the blanket according to the present invention to control body temperature of the patient under conditions of hyperthermia.

In addition, while the present invention has been particularly described by reference to a blanket having two inlets, it will be evident to one skilled in the art that any number of inlets could be provided to enable even greater flexibility of use. The placement of additional inlets is limited only by the need to maintain good air distribution and flow within the blanket. Alternatively, a single inlet could be provided.

It is also noted that it would be possible to connect a supply source of warm air to each of the inlets when using the blanket according to the present invention. Alternatively a single supply source could be connected to each inlet using a multiply branched supply hose. For example, if there are two inlets, the supply hose could have a y-shaped configuration. Each of these embodiments of using the present invention, may be advantageous in providing more even heat distribution to all parts of the blanket.

Several other alternatives to that which has been specifically described above are also within the scope of the present invention. For example, the present invention has been described as having two tear strips on both ends of the blanket. Alternatively, a single tear strip could be provided on both ends of the blanket, or a single tear strip could be provided on only one end of the blanket. In addition, more than two slits could be provided along the lower edge of the blanket, or further slits could be provided along other edges of the blanket to help with conformance of the blanket to the body of the patient. Moreover, means other than medical tape could be provided as to provide adhesion of the blanket to the patient.

The foregoing has been a description of certain preferred embodiments of the present invention, but is not intended to limit the invention in any way. Rather, many modifications, variations and changes in details may be made within the scope of the present invention.

What is claimed is:

1. An upper body blanket for use with a forced air convection system, wherein said blanket comprises an inflatable blanket having an upper end portion for positioning toward a patient's head, a lower end portion for positioning toward the lower body of the patient, and two side extensions for covering the upper torso of the patient, and further including a head fully cover the patients's face formed integrally as part of said upper end portion of said blanket and which is adapted to alternately cover or expose the patient's face.

2. A blanket according to claim 1, wherein said head cover is a convective warming head cover.

3. A blanket according to claim 1, wherein said head cover is a conductive warming head cover.

4. A blanket according to claim 1, wherein said blanket further includes at least one tie strap formed integrally as part of said extensions of said blanket.

5. A blanket according to claim 1, wherein said blanket further includes at least one slit formed in an edge of said blanket.

6. A blanket according to claim 1, wherein said blanket further includes an adhesive means formed integrally as part of said lower end portion of said blanket.

7. A blanket according to claim 1, wherein said head cover is connected to said upper end portion of said blanket along a section of said upper end portion of said blanket at a location between said two side extensions.

8. A blanket according to claim 7, wherein said head cover is a convective warming head cover.

9. A blanket according to claim 7, wherein said head cover is a conductive warming head cover.

10. A blanket according to claim 7, wherein said blanket further includes at least one tie strap formed integrally as part of said extensions of said blanket.

11. A blanket according to claim 7, wherein said blanket further includes at least one slit formed in an edge of said blanket.

12. A blanket according to claim 7, wherein said blanket further includes an adhesive means formed integrally as part of said lower end portion of said blanket.

13. An upper body blanket for use with a forced air convection system, wherein said blanket comprises an inflatable blanket having an upper end portion for positioning toward a patient's head, a lower end portion for positioning toward the lower body of the patient, and two side extensions for covering the upper torso of the patient, and further including least one tie strap formed integrally as part of said extensions of said blanket.

* * * * *